United States Patent [19]
Zelin et al.

[11] Patent Number: 5,124,661
[45] Date of Patent: Jun. 23, 1992

[54] REUSABLE TEST UNIT FOR SIMULATING ELECTROCHEMICAL SENSOR SIGNALS FOR QUALITY ASSURANCE OF PORTABLE BLOOD ANALYZER INSTRUMENTS

[75] Inventors: Michael Zelin, Plainsboro; David Jamieson, Glen Ridge, both of N.J.

[73] Assignee: I-Stat Corporation, Princeton, N.J.

[21] Appl. No.: 556,763

[22] Filed: Jul. 23, 1990

[51] Int. Cl.$^5$ .................. G01C 25/00; G01R 27/02
[52] U.S. Cl. .................. 324/601; 324/439; 422/61; 422/62; 73/1 R; 73/4 R
[58] Field of Search .................. 422/62, 61; 204/400; 73/4 R; 324/158 R, 601, 439

[56] References Cited

U.S. PATENT DOCUMENTS

| | | |
|---|---|---|
| 3,600,670 | 8/1971 | Senour et al. |
| 3,922,095 | 11/1975 | Lee |
| 4,335,349 | 6/1982 | Baldock ........................ 324/601 |
| 4,342,218 | 8/1982 | Fox |
| 4,467,273 | 8/1984 | Rudolph ........................ 340/537 |
| 4,481,804 | 11/1984 | Eberhard et al. |
| 4,518,915 | 5/1985 | Danforth .................. 324/158 R |
| 4,557,269 | 12/1985 | Reynolds |
| 4,603,574 | 8/1986 | Norman ........................... 73/4 R |
| 4,654,127 | 10/1986 | Baker |
| 4,658,829 | 4/1987 | Wallace |
| 4,672,974 | 6/1987 | Lee |
| 4,713,165 | 12/1987 | Conover et al. |
| 4,714,874 | 12/1987 | Morris ........................... 324/601 |
| 4,760,730 | 8/1988 | Frank et al. |
| 4,785,822 | 11/1988 | Wallace |
| 4,834,532 | 5/1989 | Yount |
| 4,870,347 | 9/1989 | Cicerone .................. 324/158 R |

OTHER PUBLICATIONS

ExacTech Blood Glucose Testing System User's Manual; Dec. 1987; pp. 8-11.
Corning 170 pH/Blood Gas Analyzer product literature, Dec. 1982.
Deply, D. T. et al.; "Simple zero calibrator for transcutaneous oxygen electrodes", Medical and Biological Engineering and Computing, Jan. 1988.
Calibration/Quality Control Instructions, ChemPro 500 Analyzer.
Kodak Ektachem DT product literature, Dec. 1986.
Accu-Chek II Operator's Manual, Dec. 1985, Nov. edition.
Bridges et al., "Evaluation of a new system for hemoglobin measurement", American Clinical Products Review, Apr. 1987.
Biotrack Inc., Coumatrak Protime Reagent Cartridge and Monitor Model 1000 literature, issued Jun. 16, 1987.
Sheldon, C. D. and Duggen, T. C., "Low cost Doppler signal simulator", Medical and Biological Engineering and Computing, Mar. 1987.

*Primary Examiner*—Kenneth A. Wieder
*Assistant Examiner*—Jose M. Solis
*Attorney, Agent, or Firm*—Pennie & Edmonds

[57] ABSTRACT

A reusable test unit is disclosed for testing the functionality of a portable blood analyzer, and particularly the interface between the high-impedance electrochemical sensors and the instrument. Signals are generated to simulate amperometric, conductimetric, and potentiometric sensors. Circuitry permits detection and discrimination between failures from damaged CMOS amplifiers and failures from leakage currents in contaminated connectors. The test unit may be configured to be insertable into the instrument to fit mechanically in the same fashion as a disposable sensor device. A scheme for three-dimensional routing of guard lines on a circuit board is disclosed for guarding against coupling between closely space traces and connector pads.

21 Claims, 8 Drawing Sheets

REUSABLE TEST UNIT FOR SIMULATING ELECTROCHEMICAL SENSOR SIGNALS FOR QUALITY ASSURANCE OF PORTABLE BLOOD ANALYZER INSTRUMENTS

BACKGROUND OF THE INVENTION

1. Field of the Invention

This invention relates to the quality assurance testing of instruments which read electrical signals from electrochemical sensor arrays carried on insertable sensor devices, and in particular, to a reusable test unit for use with portable battery-powered blood analyzers.

2. Description of the Problems Addressed

Portable analyzer systems, such as that disclosed in co-pending U.S. patent application Ser. No. 07/245,102 filed Sept. 15, 1988, provide challenges for quality assurance which have not been addressed in the prior art. Some of these challenges arise from the clinical setting in which the analyzer is used, and some arise from the technology employed in the system.

In a clinical setting, it has long been acknowledged that a relatively wide variation in measured values can result when identical samples are sent to different laboratories, even if each laboratory, considered individually, provides repeatable results and good internal precision. As a practical matter, variation across laboratories need not be of clinical concern for patient monitoring, if samples from a given patient are always sent to the same laboratory for testing on the same instrument. However, the convenience of a portable analyzer, and the likelihood that many such instruments may be available for use in the emergency room, in the intensive care unit, and elsewhere in the hospital or doctor's office, raise the possibility that tests on consecutive samples from the same patient may be performed with different analyzers. In that case, an unknown bias in a particular portable analyzer could be misinterpreted as a change in the patient's condition, or could mask such a change.

The diagnostic value of measurements from a portable instrument, and the reliance which a physician can place on such measurements, would be enhanced by the provision of a test unit for periodic functional testing of all the portable instruments at a particular location, to ensure that each is functioning properly and that their measurements would be in agreement within an established tolerance.

The nature of the technology employed in a portable system with disposable sensor devices can considerably compound the difficulty of providing a suitable test unit. At the outset, it should be noted that a need for frequent yet convenient and economical testing of the instrument is to be expected. If questionable results are obtained, the user needs a way to distinguish between a failure of the instrument and a defective or contaminated batch of disposable sensor devices. However, the specific implementations of the system elements, including sensors, electronic components, and connectors, each provide additional difficulties.

In particular, microfabricated electrochemical sensors (for example, those disclosed in co-pending U.S. patent application Ser. No. 07/432,714 filed Nov. 7, 1989) may be advantageous for use in disposable sensor devices, but their extremely small size leads to very weak, interference-sensitive, high-impedance signals. These signals must be amplified under demanding conditions, presenting a highly passive input to the sensor, which neither draws much current from the sensor nor permits that current to vary as the electrochemical potential from the sensor varies.

Since the portable instrument is battery powered, the amplifiers must present low power requirements. CMOS operational amplifiers are best suited to that role, but are highly susceptible to damage or performance degradation from static discharges. Consequently, an amplifier which initially provides the required input characteristics may no longer operate within specifications after continued exposure to static in normal use, and a provision for testing the integrity of the amplifiers is highly desirable.

While traditional laboratory analyzer systems present only the fluidic inputs to the user environment, the portable analyzer and disposable sensing device also expose electrical contacts. It can be expected that a clinical environment will provide frequent opportunities for contamination of contacts, through accident, misuse, or prolonged exposure to the environment in normal use. The difficulties which can arise are heightened by the small scale of the system. Input pins for the sensors are extremely close together, increasing the chances of contamination across adjacent pins leading to cross-talk between the high-impedance sensor signals.

As an aid to explanation, a typical portable instrument system is shown schematically in FIG. 1. At the left, item 110 represents an array of microfabricated sensors on a disposable sensor device. (For simplicity, only three sensors are provided in this example.) A connector 120 forms the electrical connections between the sensors and a portable instrument. Within the instrument, front end CMOS operational amplifiers 130, 140, and 150 provide low-impedance, relatively noise insensitive signals faithful to the signals from the sensors, for further processing by the instrument in circuitry (not shown) to the right of switches 160, 170, and 180. Dashed line 190 divides the Figure into two domains, and represents the interface between them. To the left is a high-impedance electrochemical domain, while to the right is a low-impedance electronic domain.

The considerations discussed above lead to a need to test on both sides of the interface indicated by line 190, including connector 120. Indeed, experience indicates that problems are more likely to occur on the sensitive electrochemical side than on the relatively more predictable electronic side.

Ideally, a test unit to solve these problems would be capable of testing elements on both sides of the interface, providing simulated high-impedance sensor signals to be passed through the connector. In addition, such a test unit would be reusable to reduce costs and be simple to operate to avoid operator error. It is also desirable that it not require the use or replacement of costly chemicals, and that it be robust to survive exposure to the clinical environment without degradation of performance. Furthermore, an optimal test unit would permit different failure modes to be readily distinguished.

3. Discussion of the Prior Art

Generally, traditional testing schemes do not directly address the problems outlined in the discussion above. For example, the software in many microprocessor-based electronic instruments includes a self-test routine which is performed at power-up or may be invoked by a user. While such a self-test routine may advantageously be employed in a portable analyzer to check many functions of the instrument, such internal testing cannot test the interface with the high-impedance electrochemical domain. To verify the performance of an instrument which measures an external physical parameter, and to test the performance of the interface through which signals are received, it is necessary to inject an externally established test signal through the interface.

Likewise, the necessary testing cannot be accomplished through common batch calibration techniques. Typically, batch calibration is accomplished by shipping a calibrator with each batch of sensors or reagents, which reflects the characteristics of that particular batch. It serves to correct the internal calibration curve used by the analyzer as appropriate for that specific batch, but it does not test the analyzer function.

One attempt to provide signal simulation for an instrument is related to U.S. Pat. No. 4,756,884 to Hillman et al. and involves capillary flow devices for optical measurement of prothrombin or clotting time. In the measurement system, sold by Biotrack, Inc. of Sunnyvale, Calif., a disposable sample card is provided with chambers through which a blood sample will flow; the sample card is inserted into an instrument which detects a change in optical density resulting from clotting. Testing is accomplished with a reusable "monitor control cartridge" (supplied with the instrument) which may be inserted in the same manner as a sample card. When a button on the monitor cartridge is pressed, an electrochromic element in the cartridge simulates the optical behavior of a blood sample, to verify that the instrument is functioning.

The monitor cartridge, however, simulates only a single optical signal. It does not emulate the high-impedance signals of electrochemical sensors, and does not test the integrity of electrical connectors or amplifiers.

Another testing technique is provided by the ChemPro system, corresponding to that disclosed in U.S. Pat. No. 4,654,127 to Baker et. al. The ChemPro analyzer provides prompts to the user to perform various steps in the measurement process. Prior to signalling the user to insert a sample card, the instrument switches on the amperometric channel normally used for glucose measurements. If an open circuit is detected, the analyzer is assumed to be functional and the user is prompted to insert the sample card. If the instrument does not detect an open circuit, the unit will not provide test instructions to the user, but instead will display instructions to insert a connector cleaning card.

That approach has only limited utility in testing the instrument-sample card interface. For example, there is no provision to test for leakage currents in all of the connector pins, a deficiency which is particularly noticed for those circuits most susceptible, namely, the potentiometric circuits. Also, testing only for an open circuit on the amperometric channel is inadequate to determine if the measurements will be accurate.

Another testing scheme for conventional analyzers is represented by the VWR brand Mini-Test Electrode Simulator. This battery powered device is intended to simulate the characteristics of a pH electrode, for testing pH meters. Switches are provided to select the pH level to be emulated, and cables are provided with connectors compatible with standard pH meters.

That electrode simulator, however, does not simulate the electrochemical characteristics of microfabricated sensor arrays, nor does it serve to test closely spaced connector pins. It also has no provision for emulating the many different sensors, which may be amperometric, potentiometric, or conductimetric, which may be simultaneously used on a single disposable sensor device.

SUMMARY OF THE INVENTION

In accordance with the preferred embodiments of the present invention, a reusable test unit mates mechanically with the connector of the portable instrument to test both sides of the interface with the high-impedance electrochemical domain. Circuitry within the unit produces signals for testing amperometric, conductimetric, and potentiometric measurement channels, without consuming any disposable sensor devices or requiring replenishment of chemicals. In the preferred embodiment, power to the unit is supplied through the connector from the instrument. Operation is under the control of the instrument, and no user controls are provided.

Test signals are provided to detect both excessive bias currents from faulty CMOS amplifiers, and leakage from contamination of the connector. By the application of a voltage step, it is possible to distinguish between the two failure modes.

The test unit may be packaged as a self-contained unit which is inserted into the instrument in the same manner in which one would insert a disposable sensor device. A plate may be provided to prevent contamination of the connector pads on the test unit. In addition, guarding of signal lines may be achieved despite extremely limited space by creating a three dimensional current path on the circuit board, using plated through-holes which are split by air gaps.

DESCRIPTION OF THE PREFERRED EMBODIMENTS

Figure 1:
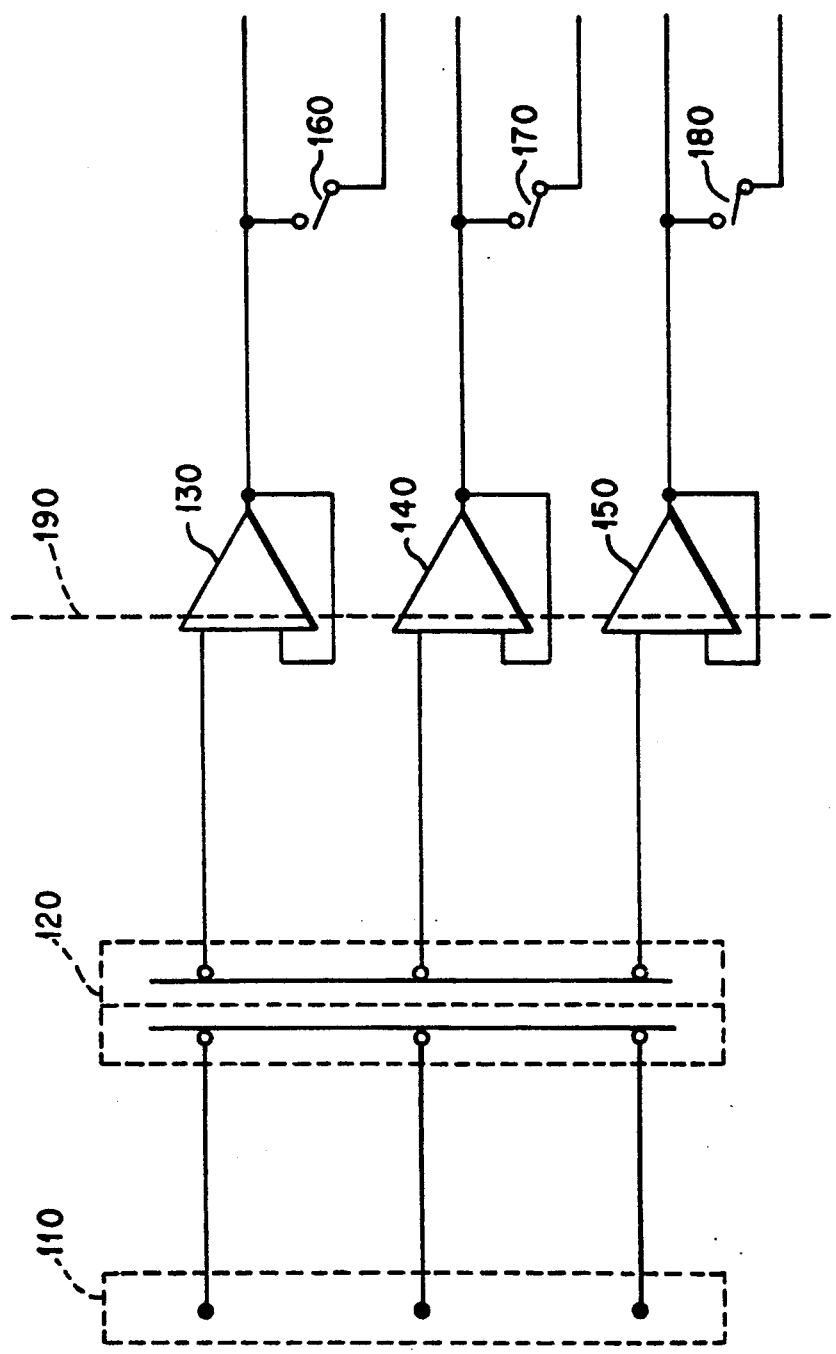
FIG. 1 is a schematic representation of the interface between a disposable sensor device and a portable instrument.

For ease of description, the preferred embodiments will be disclosed in the context of the disposable sensor device and portable instrument of co-pending U.S. patent application Ser. No. 07/245,102 filed Sept. 15, 1988, and the connector disclosed in co-pending U.S. patent application Ser. No. 07/489,844 filed Mar. 2, 1990; the disclosures of those two documents are hereby incorporated by reference. Note that each disposable sensor device may be provided with a calibrant chamber to permit sensor calibration at the time the device is inserted into the instrument; however such calibration does not provide the testing of instrument function provided by the present invention.

In the preferred embodiment, a reusable test unit contains circuitry which provides electrical signals for testing instrument function. Because the signals are produced by electrical circuitry which simulates the operation of chemical sensors, but does not employ actual sensors, no chemicals are used and no disposable sensor devices need be consumed for testing. Consequently, the test unit may used repeatedly without replenishment of supplies and with resulting advantages in economy.

1. Instrument Failure Modes

Two important failure modes must be detected and distinguished by the test unit. One is loss of electrical isolation between neighboring channels in the connector. If undetected, decreasing isolation will permit increasing leakage currents to flow between neighboring channels, leading to erroneous measurement results on both. Failure of this "crosstalk" variety may be detected as a voltage drop across large series resistors provided in the test unit.

Another failure mode arises from static electricity damage to the high-impedance CMOS operational amplifiers in the instrument. The design of the connector, which includes a shorting bar for static protection, reduces the likelihood of damage, and the inputs to the amplifiers are also protected by diode pairs, but notwithstanding these measures, both the diodes and the field effect transistors are prone to damage. Dielectric materials within these CMOS devices can break down as a result of static, giving rise to leakage currents, which leads to increased bias current at the inputs to the amplifiers.

Excessive bias current poses significant problems. In the case of an amperometric sensor, a degradation of CMOS amplifier devices can cause variable bias currents. This will give rise to a variable offset in the calibrant and sample currents which can undermine the utility of the analytical information which could otherwise be derived from the ratio of those two values. For potentiometric sensors, the bias current may be sufficiently substantial to polarize the membranes of sensors. Since potentiometric sensors are designed for low current flow, their functionality can be unacceptably impaired by such polarization. Large series resistors in the test unit can be used to detect a voltage drop between the voltage generated by the test unit and the voltage detected by the instrument, indicating excessive input bias current.

One particularly useful technique for testing potentiometric channels provides both accuracy and the ability to discriminate between failure modes, by applying a known step in voltage across two input channels. The enhanced accuracy may be understood by recognizing that all CMOS amplifiers will have a small yet non-zero input bias current. If only one voltage is measured, the sensitivity of the determination is limited by the voltage drop caused by the finite bias current flowing across the large series resistor of the test unit. However, this sensitivity limitation can be overcome by measuring a voltage step, because the bias current is essentially constant.

Discrimination between excessive bias current and loss of electrical isolation between neighboring channels can also be achieved by applying a voltage step. Suppose, for example, that the values of two applied voltages as measured by the instrument are incorrect, but that the difference between them (the step size) is accurately measured. In that case, the failure mode is readily identified as excessive bias current, probably resulting from damage to a CMOS amplifier. The ability to distinguish this failure mode is important, because the instrument requires repair after such a failure.

In contrast, if reduced isolation is detected, the user may be able to cure the problem immediately by simply cleaning the connector to remove contamination. Most importantly, if no failures are detected, the instrument can be relied upon to operate within specifications.

2. Test Unit Circuitry

In the preferred embodiment, the test unit is adapted to connect to connector pins of the instrument, in much the same manner that a disposable sensor device would be connected. A typical configuration may include a set of sixteen closely spaced connector pads. A suitable assignment scheme for the pads is reflected in FIG. 2, where each of lines 210 is marked with a signal identifier corresponding to a connector pad to which it is connected. In this scheme, the first, second, fifteenth, and sixteenth test unit pads serve to provide coded identification information for the instrument, to indicate that the item connected is the test unit, rather than a disposable sensor device. Details of the coding scheme are explained in the connector disclosure referred to above.

Disposable sensor devices may vary in the selection and number of sensors they carry, so identification of the particular device is necessary to permit the software in the instrument to interpret properly the signals. For the test unit, the coding information indicates to the measurement software that testing is to be done on the various channels according to the predetermined assignment scheme.

Figure 2:
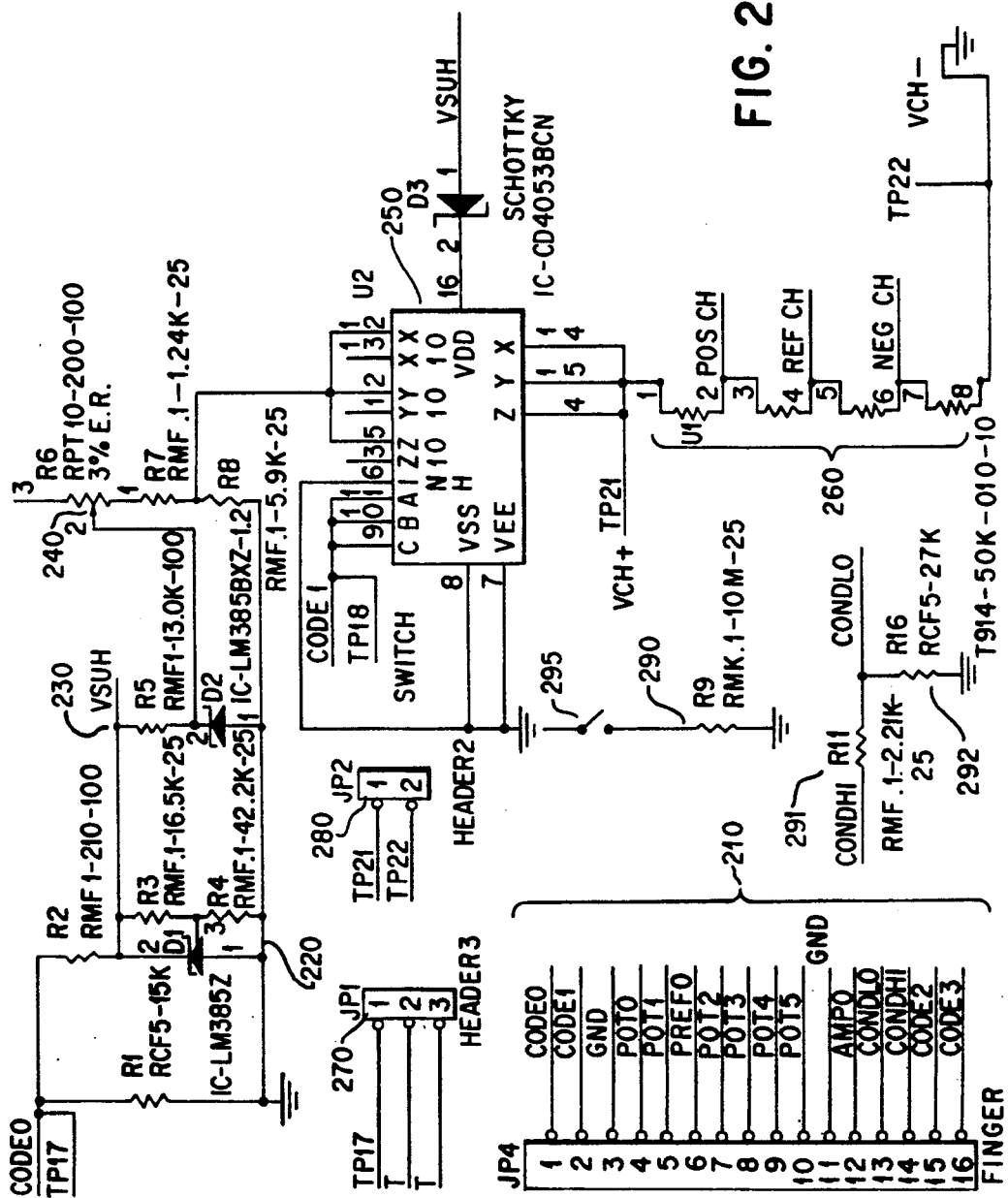
FIG. 2 is a schematic of test unit circuitry according to the present invention.

For the scheme reflected in FIG. 2, the fourth, fifth, and seventh through ninth pads correspond to potentiometric sensors (POT0 through POT5), while the third and eleventh pads are assigned to ground (GND). A connection to a reference electrode is represented by the sixth pad (PREF0), and an amperometric sensor by the twelfth pad (AMP0), while the thirteenth and fourteenth pads are provided for emulation of conductimetric sensors (CONDLO and CONDHI).

Circuitry for producing the signals to be passed through the connector is also shown in FIG. 2. Provisions for testing potentiometric, conductimetric, and amperometric sensor channels will be explained in that order.

Given that all potentiometric channels are measured versus the reference channel (PREF0) it is necessary to determine the bias current of this channel. This can be achieved by measuring PREF0 bias versus the ground (either the third or eleventh of lines 210).

The voltage source for testing potentiometric sensors is derived from the instrument, through one of the coding pins (as illustrated, CODE0). Typically, this will be five volts, although some variation from instrument to instrument is to be expected. The battery based power supply of the instrument thus provides all power to the test unit, and no separate battery for the test unit is required. In this example, two voltage regulation stages 220 and 230 will provide approximately 1.2 volts to trimming potentiometer 240, and trimming is set to yield 1 volt at the output of switch 250 (when closed) to matched resistors 260. Headers 270 and 280 are provided to break out voltages at appropriate nodes to facilitate trimming.

Figure 3:
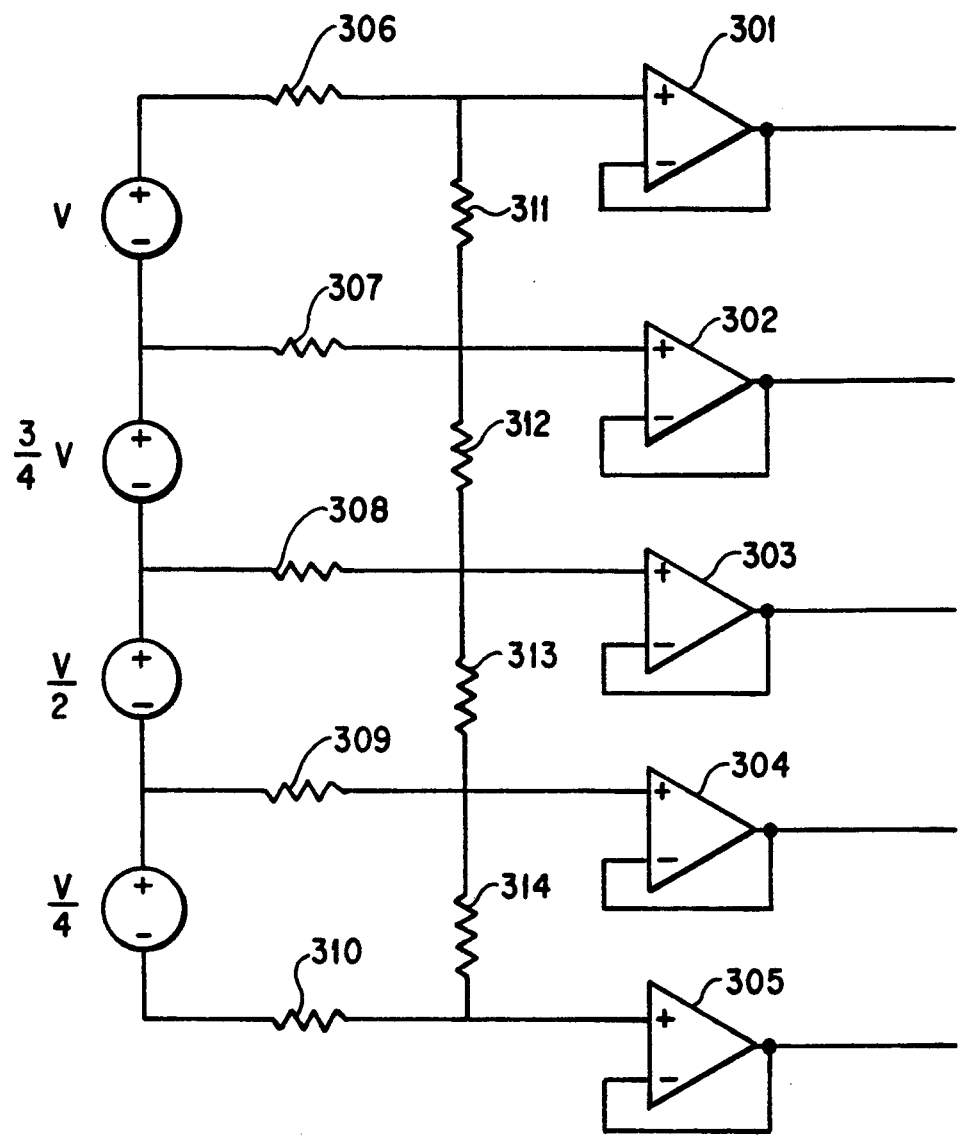
FIG. 3 is a schematic model of potentiometric channel testing.

Several potentiometric channels may be tested with respect to a common reference electrode channel by use of a high precision resistor chain. Voltages from consecutive nodes between resistors 260 will differ by V/4, where V is the voltage output from switch 250. Voltage from these nodes may be applied to resistors which simulate sensors. The simulation may be understood by reference to a simple model of the instrument system as shown in FIG. 3. There, a CMOS front end operational amplifier 303 for a reference channel is shown, along with amplifiers 301, 302, 304, and 305 for potentiometric channels.

Resistors 306 through 310 are used to simulate high-impedance microfabricated sensor electrodes. For example, 306 may correspond to an electrode to measure ammonium ions, while 307 through 310 correspond to potassium ion, reference, chloride ion, and sodium ion electrodes, respectively. Resistors 311 through 314 are drawn in this model to represent possible leakage paths between neighboring channels. In this example, for a fixed applied voltage V, the potential between either of the outermost channels and the center reference channel should be V/2, while the potential between the inner channels and the reference channel should be V/4. The expected voltage between other pairs is also readily derived. Any leakage between the channels will produce voltages differing from the expected values, which can be easily detected in the instrument.

For this test to be of utility, the applied voltage V provided by regulation stages 220, 230 and trimming potentiometer 240 must agree within certain tolerances with voltage references within the instrument, that is, both the test unit and the instrument must measure voltage to the same standard.

It is clear that the combined tolerances of the signal simulator and the instrument should be of sufficient resolution to determine whether the instrument is within specifications. (Although tolerances are discussed here with respect to potentiometric circuits, the general form of analysis applies to amperometric and conductimetric circuits as well.) The total system tolerance will be the sum of the tolerance to which the test unit can produce a step change in voltage and the tolerance to which the instrument software and hardware can reproduce a signal that appears at the input.

The tolerances to be considered for the test unit include the resistor chain, large value resistors, temperature dependence of the components, leakage of analog switches, and power supply rejection ratio. For the instrument the important tolerances are noise, accuracy of the components, electronic discretization, and mathematical truncation of the data.

The number of channels which may be tested by the foregoing scheme is limited, since as the number n of channels to be tested increases, the smallest voltage to be measured V/n may become too small, particularly at high gain where V may be much less than one volt. A variation on that scheme permits an unlimited number of channels to be tested with high resolution.

Figure 4:
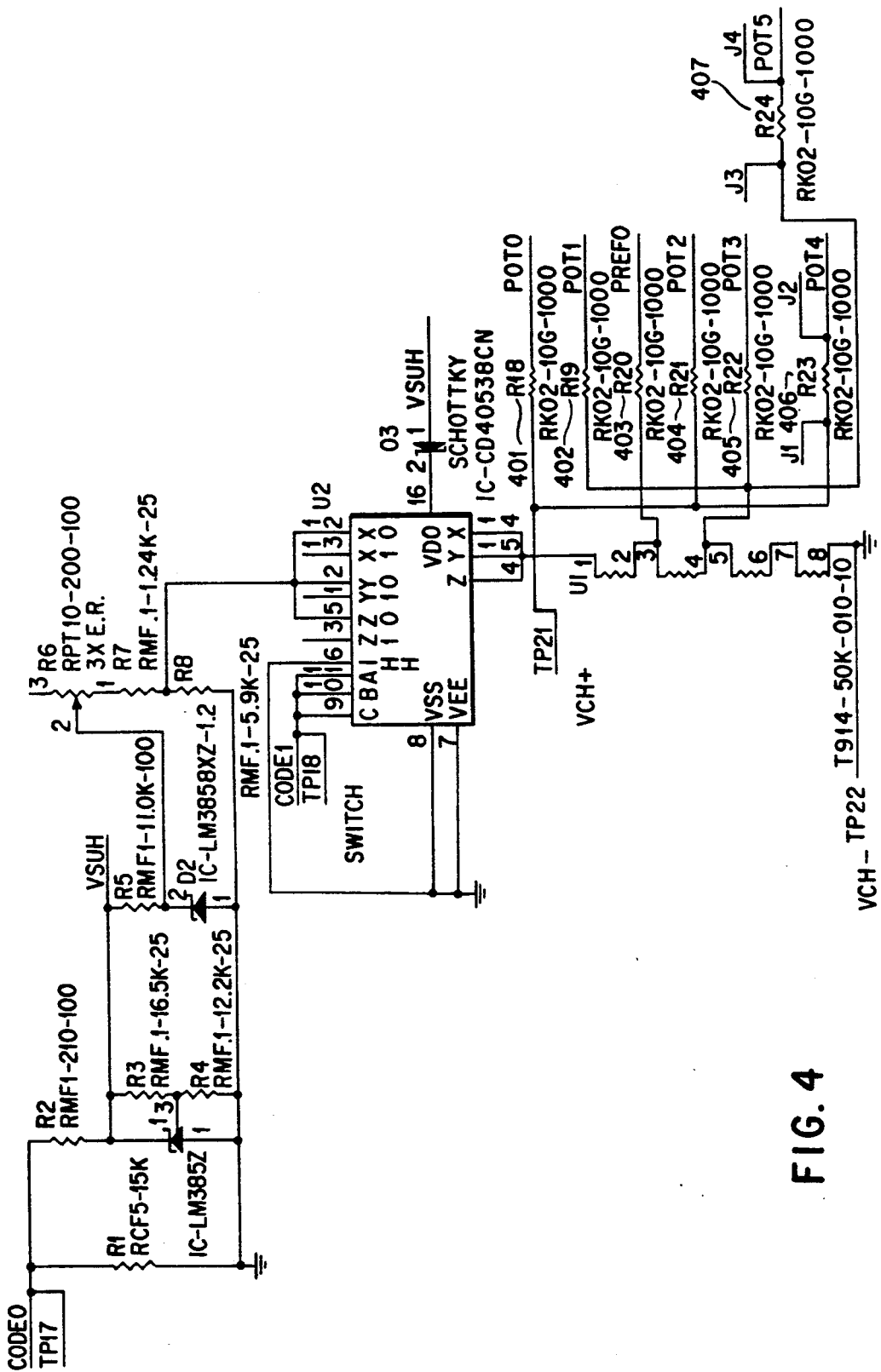
FIG. 4 is a schematic of alternative potentiometric channel test unit circuitry.

As shown in FIG. 4, resistors 401 through 407 are provided to simulate high-impedance sensor electrodes, but are connected in a manner which avoids resolution difficulties. In this embodiment, at some predetermined gain a voltage of zero volts is applied to the reference channel, with +V and −V applied alternately to channels on either side. In the absence of leakage currents, the voltage difference between the reference channel and all others will be either +V or −V, and the voltage between adjacent channels should be +2V or −2V. Deviations indicative of leakage can be easily detected.

Although resolution limits are overcome by this scheme, the capability to measure leakage between channels of the same polarity is lost. In practice, this is not a significant problem, because channels of the same polarity are not adjacent. Experience shows that the most common leakage path is between adjacent channels, typically by contamination across neighboring connector pins. Contamination which might bridge from one pin to a non-adjacent pin, skipping pins in between, is considerably less likely.

It is essential that the circuit design and selected components be of sufficient quality to ensure that the desired voltage is maintained across the resistor chain, independent of variations in the supply voltage and temperature. If a CMOS analog switch is used for switch 250, its impedance variation with temperature and voltage supply must be negligible with respect to the impedance of the resistor chain.

Conductimetric measurements are useful for determining hematocrit. Typically, the measurement will use two electrodes exposed to the blood sample, with one operated in an a.c. mode and the other tied to ground. The a.c. voltage is related to the impedance of the sample medium between the two electrodes. In the instrument, the a.c. voltage may be converted to a positive d.c. voltage by taking the modulus of the signal and then applying a low pass filter.

To simulate the signal obtained in blood for testing instrument function, a precision resistor with a value equivalent to that of the impedance of blood for a given electrode geometry may be used. The measured d.c. voltage at this impedance can be compared to the stored expectation value in the instrument to determine whether the circuitry is operating within specifications. In FIG. 2, a suitable 2.21 kOhm 0.1% resistor for this purpose is shown as resistor 291. Resistor 292 is provided to avoid defeating shielding of the test unit when conductivity is not being a measured and an open circuit would otherwise expose the unit to interference. If multiple conductivity measurements are required, a resistor is engaged between each a.c. mode output and a ground (the ground may be common).

Alternatively, a channel may be tested with two resistors of different values, so that two values can be calculated and compared to multiple expectation values. The disadvantage of this approach is the necessity to provide some method of switching between the two resistors, and the concomitant increased complexity of the test unit circuitry. If an electronic switch is selected, a negative power supply is necessary.

In principle, any sort of network of known impedance could be used for signal simulation. However, obtaining the required precision with available capacitor or rectifier components is not practical, and the resistor embodiments are preferred for that reason.

Those skilled in the art will recognize that high frequency a.c. measurements must be protected from stray capacitive coupling, through careful circuit design and guarding of signal lines where possible. Guarding provisions will be discussed in fuller terms below.

Amperometric sensors may be used, for example, to test for glucose. If an excessive bias current is present from a damaged operational amplifier, it will offset and make unreliable the measured current signal. Similarly, contamination between connector pins will provide a parallel current path so that the true behavior of the sensor is not seen.

Ideally, a simulated signal would provide substantially the same magnitude current as an actual sensor. In the preferred embodiment, the sensor response is simulated by a single resistor connected between the working electrode and the reference electrode; such a resistor is shown in FIG. 2 as resistor 290.

The applied potential in the actual measurement is set digitally in the instrument to a bit resolution of 2 mV, or 0.5% error. A typical current value in the expected range can be achieved with a 10M Ohm resistor. Preferably, a 0.1% precision resistor is chosen with a good temperature coefficient (for example 0.025% per degree C) so that the precision of the resistor is better than that of the applied potential. It is desirable that the total imprecision (in this example, 0.625%) be roughly an order of magnitude less than that of the inherent imprecision of the actual sensor to be simulated. If these guidelines are followed, both the current and the applied potential can be tested in a simple and reliable manner.

Ordinarily, the source of the applied potential is a sample and hold circuit with in the instrument. Testing can determine both the accuracy of the potential, and the droop rate (slope) as the potential varies with time from leakage through the analog switch, leakage across the sample and hold capacitor, and the input bias current of the voltage follower operational amplifier.

Improved sensitivity to leakage in amperometric channels can be achieved by the inclusion of an analog switch 295 which can be either open or closed during use of the test unit. Any leakage current greater than that associated with an open circuit analog switch is then measurable accurately. This can be accomplished by making a current measurement at two different voltages to eliminate the variable offset of the CMOS amplifier. The time variation of the offset will not distort the measurement if the two current measurements are taken in quick succession.

If an array of amperometric sensors must be simulated, resistors with appropriate values are chosen for each. If a common reference electrode is used, the resistors are engaged between the common reference and the appropriate sensor.

Other circuits may also be used to provide a fixed current source, at the expense of more complex circuitry. In addition, using a fixed current source does not permit checking of the applied potential for actual measurements.

3. Packaging

If desired, the test unit circuitry can be constructed as an auxiliary circuit board within the test instrument itself. By providing a mechanism to move the instrument connector optionally into contact with the test unit (instead of into contact with a disposable sensor device), simulated signals can be injected through the connector, providing testing of the interface which software self-test routines cannot provide. One disadvantage of this approach is that the same test unit cannot be used with multiple instruments. The complexity of each instrument is increased not only by the inclusion of the test unit but also the mechanism for optional connector motion.

Figure 5:
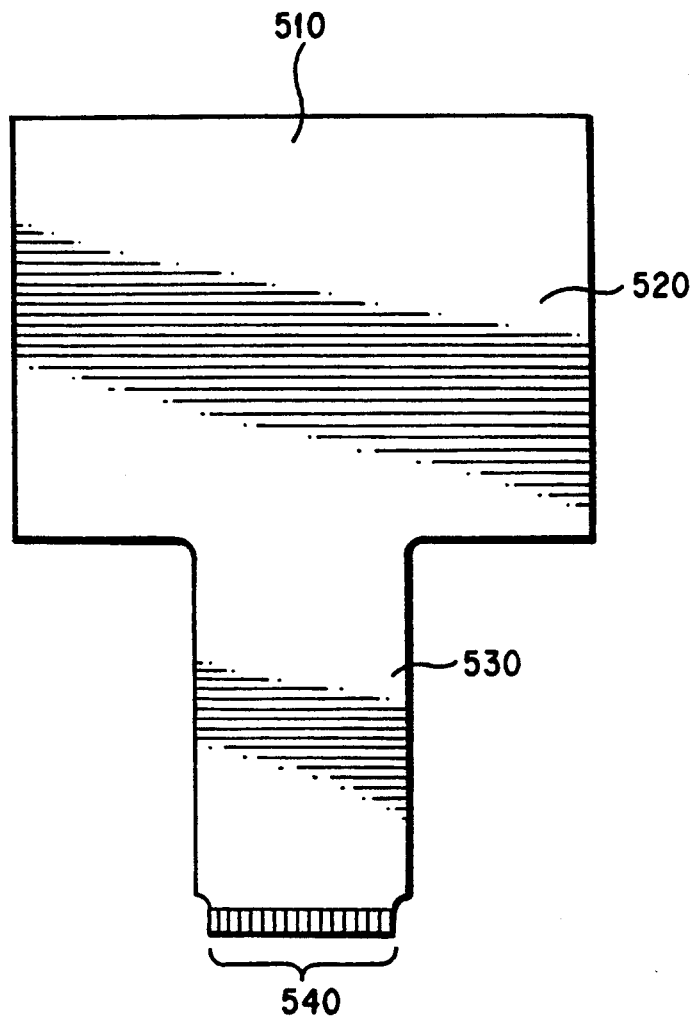
FIG. 5 shows a preferred circuit board shape.

In the preferred embodiment, the test unit is packaged for insertion into an instrument through the same port which accepts disposable sensor devices. The test unit is shaped such that one end mimics the shape of a disposable sensor device to mate mechanically with the instrument connector. As shown in FIG. 5, a circuit board 510 is provided with a broad area 520 to carry the necessary precision resistors, switch, connecting traces, voltage regulating components, and so on, and a narrow finger 530 which bears contact pads 540 for mating with the pins of the instrument connector.

Figure 6:
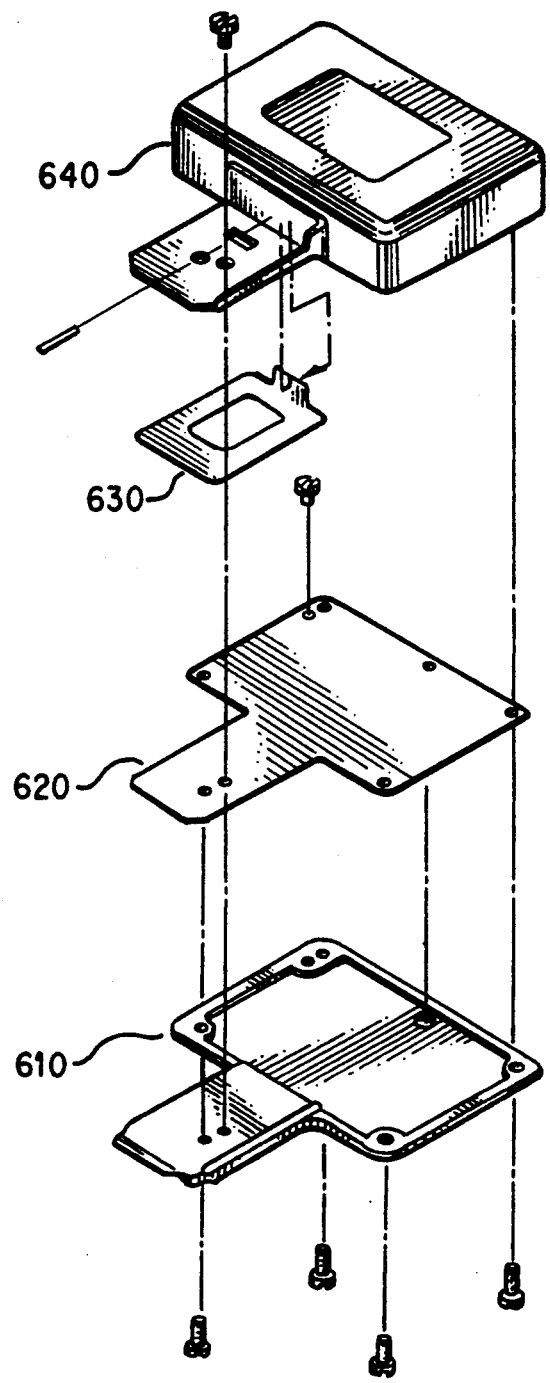
FIG. 6 shows a preferred test unit packaging.

FIG. 6 illustrates the preferred construction for a complete test unit with case. A base 610 supports circuit board 620 (electronic components are not shown). A cover 640 is held onto the base by screws. Plate 630 is provided to protect the contact pads at the narrow finger of the circuit board. To prevent contamination the plate is held forward by spring action, reducing the likelihood that fingerprints or spilled fluids will reach the contact pads. Upon insertion into the instrument, the plate will be displaced backward by the structure of the instrument, exposing the contact pads for mating with the instrument connector pins. As an additional safeguard against contamination bridging neighboring contact pads, the circuit board may be cut to leave small gaps between adjacent pairs.

The preferred packaging provides a shielded box for the test unit, to prevent the pick up of interference. When the test unit is inserted into the instrument, the mechanical connection to the structure of the instrument connector will establish a common ground.

No switches or controls of any description are found on the test unit case. In operation, the user need only insert the test unit into the instrument to be tested. By virtue of the coding information from the connector pins, the test unit is recognized by the instrument, and the test regimen can be completely automatically controlled by the measurement software in the instrument. The instrument then interprets the signals received and can display appropriate messages to the user, indicating, for instance, that the instrument should be taken out of service, or that the connector should be cleaned and the test repeated.

4. Signal Line Guarding

The close spacing of contact pads in the test unit and of the traces connecting to them presents special difficulties for avoiding contamination and for guarding of signal lines. Where possible, a guard conductor can be placed to surround an element and separate it from neighboring features. However, the contact pads are not amenable to such a solution because there is inadequate room.

Surprisingly, this problem is compounded if the circuit board is cut as described above to provide contamination-inhibiting gaps between adjacent contact pads. It would ordinarily be expected that cutting the board would give rise to a very high bulk resistance between pads from the resistance of the air. In addition, the surfaces of the sides of each cut provided an extended path length between neighboring pads, which would be expected to increase resistance.

However, the exposed sides of the cuts in the circuit board can be sufficiently hydrophilic that a leakage path is produced along the cut which can be of significant concern. Although the path between pads may be longer, the net effect from moisture affinity of the fibers of the circuit board may be to reduce resistance. Treatment of the surface of the cut with a material such as Teflon may aid in reducing the hydrophilic behavior of the cut. However, in the preferred embodiment, this problem is solved by the use of guard lines with an unusual three-dimensional arrangement.

Figure 7:
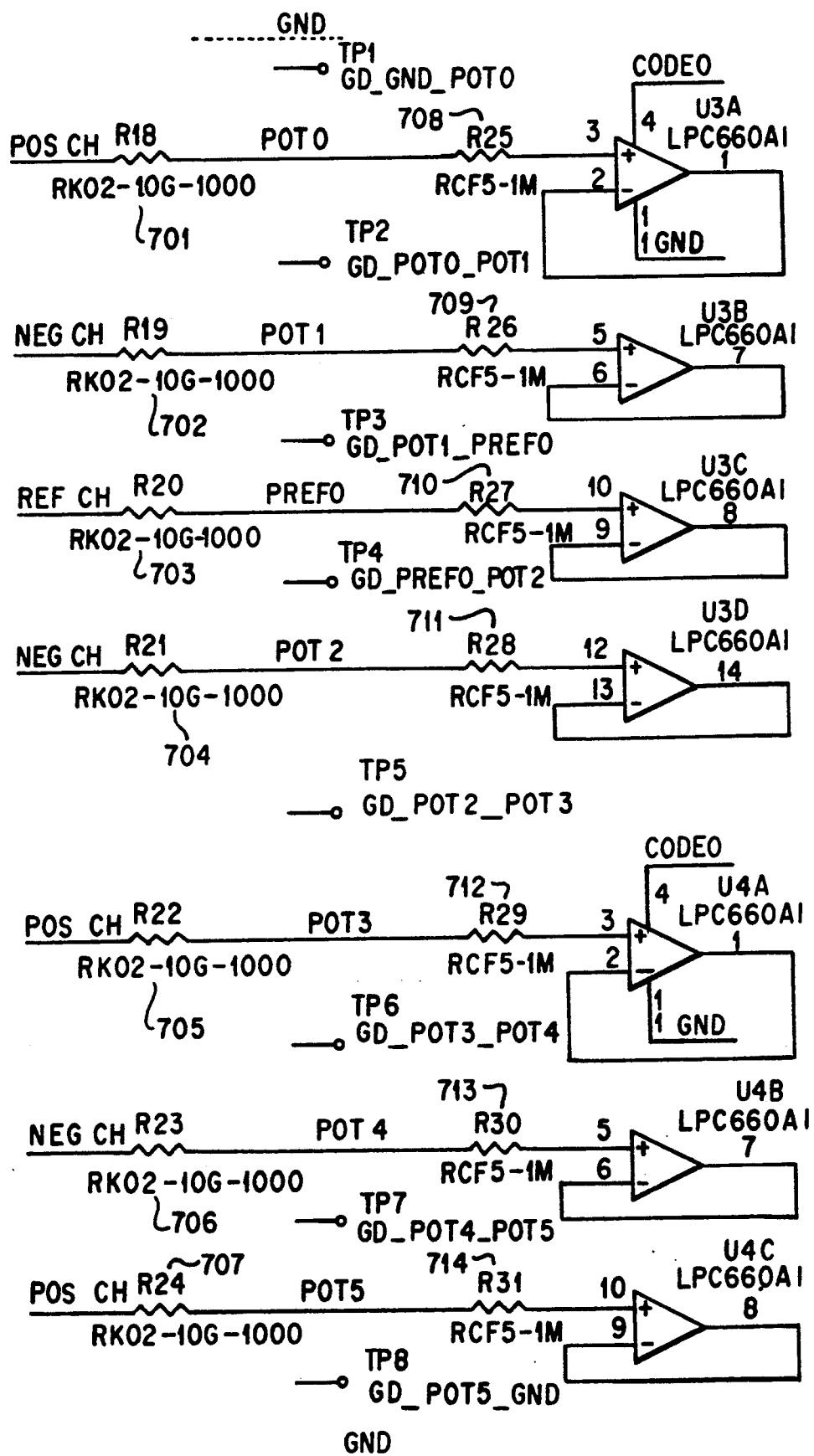
FIG. 7 is a schematic of guard line circuitry.

As shown in FIG. 7, circuitry is provided in the test unit to provide guarding of the traces and contact pads for several channels. Resistors 701 through 707 correspond to resistors 401 through 407 of FIG. 4. Guard lines may be provided to accompany each trace, and can be held at substantially the same potential as the traces they protect, by appropriately connected operational amplifiers. Placement of the guard lines between traces greatly reduces the likelihood of leakage from one trace to another.

Figure 8:
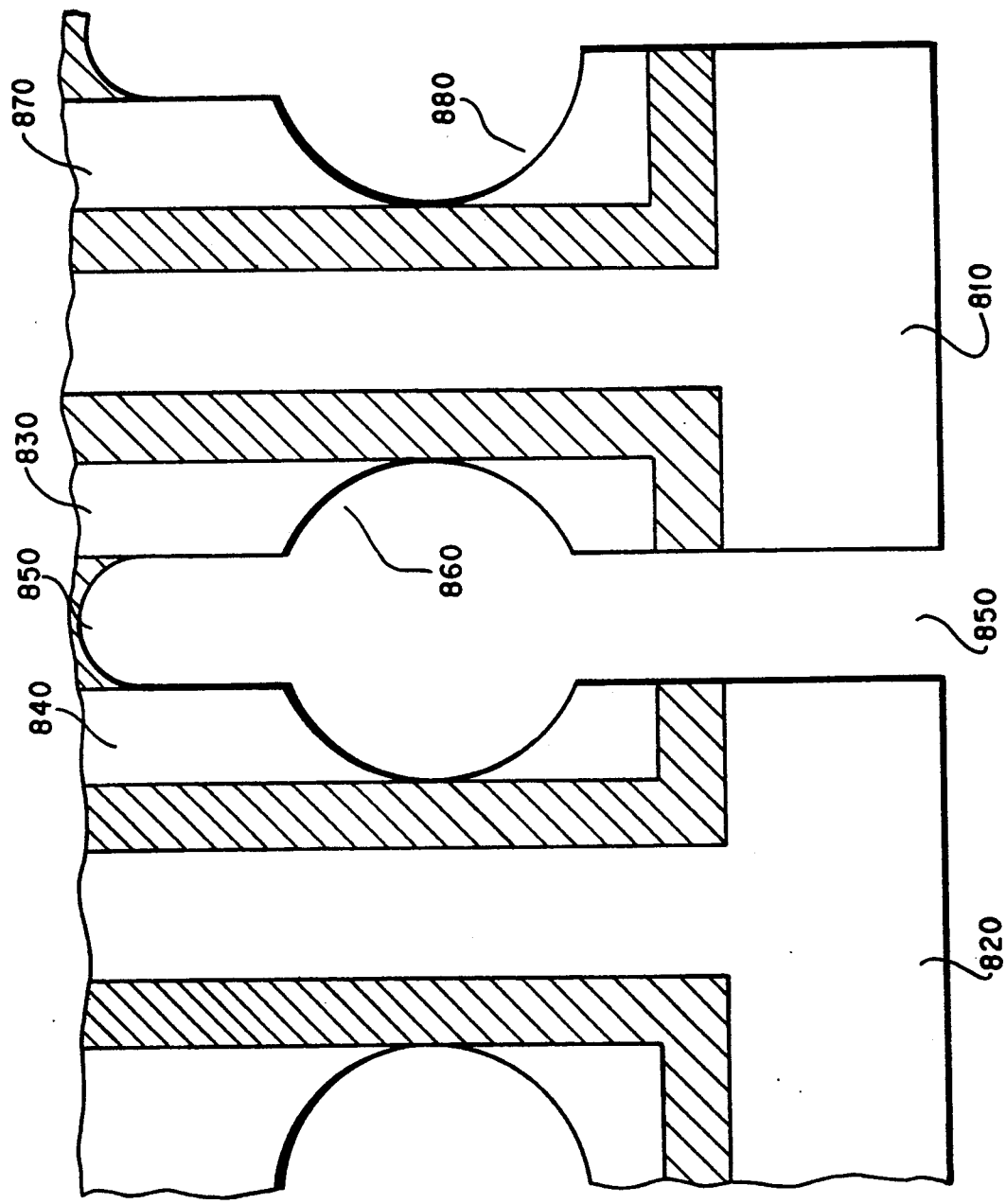
FIG. 8 is a diagram of a guard line layout scheme.

The geometry of the guard lines can be understood by reference to FIG. 8, which represents a top view of a portion of the protruding finger of the circuit board. Connector pads 810 and 820 are protected by guard lines 830 and 840 respectively. Cut 850 is intended to prevent contaminants from connecting pads 810 and 820, but offers a leakage path along its vertical edges perpendicular to the horizontal plane of the circuit board surface. To prevent leakage, a hole 860 has been drilled and through-plated prior to making cut 850. The horizontal conductor of guard line 830 is thus extended vertically by the remaining plated portion on the right side of hole 860, interrupting any leakage path along the vertical sides of cut 850.

On the underside of the circuit board, a thick conductor (not visible) is placed beneath pad 810 to connect guard line 830 with line 870 which has similarly been extended vertically through the left side of through-plated hole 880. Effectively, a continuous guard line has been provided for pad 810 which protects its trace on the upper horizontal surface of the board, descends via the surface of through-plated hole 860 to prevent leakage through cut 850, continues in the form of a thick conductor pad on the bottom surface of the board, rises once more via through-plated hole 880, and again runs along the upper surface of the board as line 870. A thick pad is preferred to isolate the sides of the cut vertically from the base beneath the circuit board, to prevent creation of an additional path for leakage along the surface of the base.

To protect the integrity of the guard scheme, plate 630 also serves to reduce the likelihood of static discharge damage to the operational amplifiers shown in FIG. 7. In addition, resistors 708-714 are provided for extra static protection of the amplifiers; diodes in the amplifiers are relatively small and hence susceptible to damage.

5. Mechanical Considerations

A variety of mechanical difficulties and failures can also be anticipated. These include failure of the test unit to correctly engage the instrument connector, misalignment of the test unit with respect to the instrument connector, damaged or broken contact pins in the instrument, non-functional coding pins, and failure of the mechanism to be grounded with respect to the ground of the instrument. Any of these events will give rise to partial or complete inability of the test unit to communicate with the instrument, so that the system failure will be apparent.

While the invention has been described in conjunction with specific embodiments, it is evident that there are numerous variations which will be apparent to those skilled in the art, in light of the teachings of the foregoing description.

We claim:

1. A reusable test unit for quality assurance testing of a portable analyzer instrument, the instrument having a multi-channel connector for electrical connection to a disposable sensor device and front end amplifiers for receiving signals from said multi-channel connector, comprising:

connector means for establishing electrical connection with the multi-channel connector of the instrument;

simulated signal means for simulating on separate channels a plurality of microfabricated electrochemical sensors, each having a relatively high impedance with respect to the outputs of said front end amplifiers;

means for enabling detection of instrument failures arising from said multi-channel connector; and means for enabling detection of instrument failures arising from said front end amplifiers.

2. The reusable test unit of claim 1 wherein the simulated signal means simulates a combination of amperometric, potentiometric, and conductimetric sensors.

3. The reusable test unit of claim 1 wherein the simulated signal means further comprises means for applying a known voltage between a potentiometric channel and a reference channel.

4. The reusable test unit of claim 3 wherein the simulated signal means applies voltages, of opposite polarity with respect to the reference channel, to adjacent potentiometric channels.

5. The reusable test unit of claim 1 wherein the simulated signal means further comprises means for establishing a known current between an amperometric channel and a reference channel.

6. The reusable test unit of claim 5 wherein the means for establishing a known current applies a voltage across a resistor between the amperometric and reference channels.

7. The reusable test unit of claim 1 wherein the simulated signal means further comprises means for applying a know impedance between two conductimetric channels.

8. The reusable test unit of claim 1 wherein the test unit is provided as a circuit board within the instrument.

9. The reusable test unit of claim 1 further comprising a case for containing the simulated signal means, having a protrusion carrying the connector means and adapted for insertion into the instrument.

10. The reusable test unit of claim 9 further comprising retractable plate means for protecting the connector means from contamination.

11. The reusable test unit of claim 1 further comprising leakage measuring means for measuring leakage of the multi-channel connector.

12. The reusable test unit of claim 1 further comprising bias current measuring means for measuring bias current of a front end amplifier within the instrument.

13. The reusable test unit of claim 11 further comprising failure distinction means for distinguishing failures of the instrument arising from leakage of the multi-channel connector from failures arising from excessive bias current of a front end amplifier within the instrument.

14. The reusable test unit of claim 12 further comprising failure distinction means for distinguishing failures of the instrument arising from leakage of the multi-channel connector from failures arising from excessive bias current of a front end amplifier within the instrument.

15. The reusable test unit of claim 1 further comprising means for applying a known step change in voltage between two channels.

16. The reusable test unit of claim 1 further comprising identification means for providing electrical signals to the instrument to identify that the test unit is connected.

17. The reusable test unit of claim 1 wherein the test unit is powered by the instrument through the connector means.

18. The reusable test unit of claim 1 wherein the connector means includes a plurality of connector pads on one surface of a circuit board, the circuit board being cut to provide air gaps between adjacent pairs of connector pads.

19. The reusable test unit of claim 18 further comprising guard lines on the circuit board of the connector means on the same surface as the connector pads, to inhibit leakage currents.

20. The reusable test unit of claim 19 wherein a plated through-hole in the circuit board is split by one of the cut air gaps, the remaining circumferential plated surface on one side of the hole being connected to one of the guard lines.

21. The reusable test unit of claim 20 further comprising a conductor placed on the opposite surface of the circuit board from the connector pads and connected to the remaining circumferential plated surface on the one side of the hole.

* * * * *